United States Patent [19]
Baumann et al.

[11] Patent Number: 5,667,504
[45] Date of Patent: Sep. 16, 1997

[54] PROCESS FOR THE ADJUSTMENT OF A SWITCHABLE FLOW LIMITING APPARATUS, AND AN APPARATUS OPERATING ACCORDING TO THE PROCESS

[76] Inventors: Hans Baumann, Bahnhofstrasse 12a, 24223 Raisdorf; Karl-Heinz Otto, AmHochbehalter 13, 24146 Kiel; Kai-Jurgen Hinrichs, Holtenauer Strasse 116, 24118 Kiel; Wolfgang Graczyk, Randersstrasse 2, 24109 Kiel; Jorg-Roger Peters, Dorfstrasse 20, 24241 Schmalstede, all of Germany

[21] Appl. No.: 321,638

[22] Filed: Oct. 11, 1994

[30] Foreign Application Priority Data

Oct. 8, 1993 [DE] Germany ............... 43 34 247.7

[51] Int. Cl.⁶ ........................................... A61K 9/22
[52] U.S. Cl. .................. 604/891.1; 604/152; 128/903
[58] Field of Search ................... 604/65, 66, 67, 604/131, 152, 891.1, 249; 128/903; 607/32

[56] References Cited

U.S. PATENT DOCUMENTS

| | | | |
|---|---|---|---|
| 4,146,029 | 3/1979 | Ellinwood, Jr. .............. | 128/903 X |
| 4,731,051 | 3/1988 | Fischell ......................... | 604/67 |
| 4,808,089 | 2/1989 | Bachholtz et al. ............. | 604/152 X |
| 4,987,897 | 1/1991 | Funk .............................. | 607/32 X |
| 5,089,017 | 2/1992 | Young et al. ................... | 623/3 |

FOREIGN PATENT DOCUMENTS

| | | | |
|---|---|---|---|
| E6592 | 6/1984 | Austria ......................... | A61M 1/00 |
| 0128703 | 12/1984 | European Pat. Off. ........ | A61M 5/14 |
| 293055 | 10/1983 | Germany ...................... | A61M 5/14 |
| 3316934 | 11/1983 | Germany ...................... | A61F 1/00 |

*Primary Examiner*—Mark Bockelman

[57] ABSTRACT

A process and an apparatus for adjustment of a switchable, flow-limiting device for limited flow of liquids or gases employs a remote service device. The flow-limiting device and the service device are spatially separated and there is no bodily connection between the two. Energy necessary for adjustment of the flow-limiting device is transmitted from the service device into an infusion pump that contains the flow-limiting device. The flow-limiting device is a valve having three stable operating positional states. The valve can only be switched while energy is being transmitted from the service device.

12 Claims, 4 Drawing Sheets

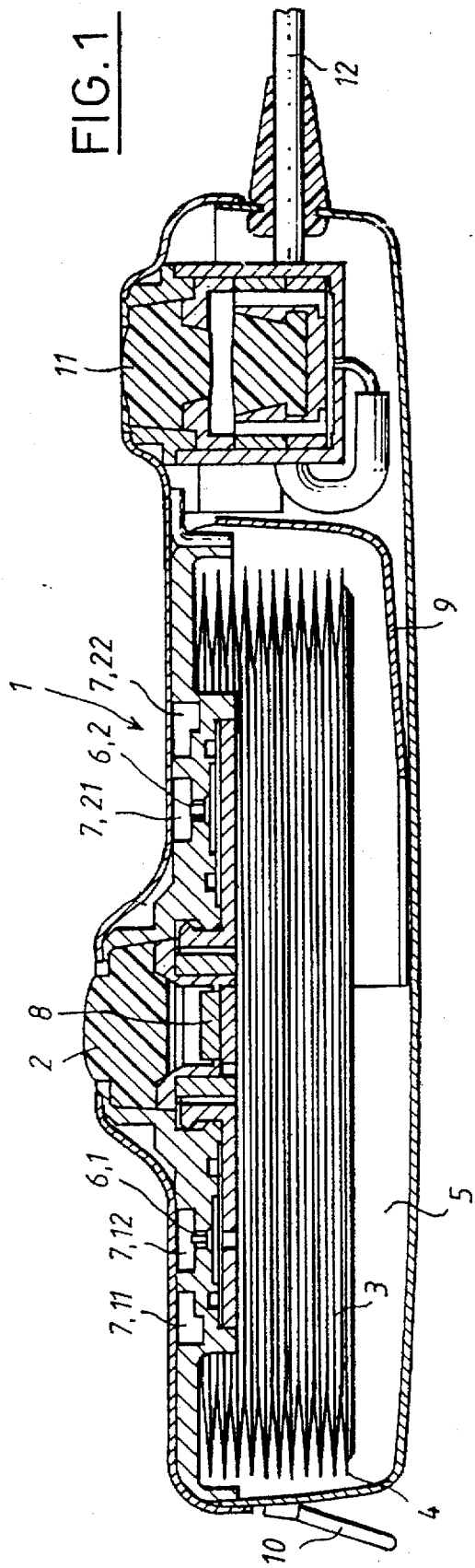

PROCESS FOR THE ADJUSTMENT OF A SWITCHABLE FLOW LIMITING APPARATUS, AND AN APPARATUS OPERATING ACCORDING TO THE PROCESS

BACKGROUND OF THE INVENTION

1. Field of the Invention

The present invention relates to processes for a switchable flow-limiting apparatus for limiting the flow of liquids or gases in a patients body, and an apparatus which operates according to the process.

Such apparatuses are used for very varied applications. It is particularly difficult if these apparatuses when in use can no longer be manually adjusted without further action. Particularly for infusion equipment, it is required that the devices furthermore operate absolutely reliably, since a person's life depends on their functional capability. For this reason, the concern in what follows will primarily be with apparatuses which are suitable for use in infusion equipment. However, this is not to preclude the application of the invention to other fields of use.

2. Relevant Prior Art

Infusion systems which are implanted into the body of a patient are already known. They are used for the controlled administration of medicaments. Implantable infusion devices, also termed infusion pumps or medicament pumps, have particular uses in the following aspects of the case: spastic therapy, pain therapy, chemotherapy, and so on. They make possible a direct, continuous administration of medicament (for example, Baclofen or morphine) into the arterial or venous system, and also into the epidural or intraspinal space of the human body. The kind of medicament supply permits such a small dose (0.5–3 ml per 24 hours) that the patient's quality of life is still maintained while the organism is spared side effects which burden it, such as are known in the usual therapies (tablets, drops, injections).

Implantable infusion devices with a fixed, predetermined flow rate have the disadvantage that when the aspects of the case of the patient changes such that a greater or smaller medicament requirement is needed, after implantation of the device, a very expensive pump removal and re-implantation has to be undertaken in order to maintain the patient's quality of life.

Furthermore, it is desired in connection with certain therapies to vary the amount of the medicament which is delivered in a unit of time.

Implantable infusion devices with a battery as an energy source are partially equipped with a controllable flow rate and are electronically controlled. These infusion devices have a normal life, which is limited by the life of the energy supply, of about 36 months in the body of the patient. After that, the removal of the pump is necessary in order to renew the energy source. Thus the duration of functioning of the implant is limited to a relatively short time by the limited life of the energy storage unit (battery or accumulator). These appliances moreover have a very expensive control appliance, which is for the most part considered to be operator-unfriendly, and with which the physician can newly provide the changes and cycles of the flow rate, according to a program.

Legal determinations, for example in Germany, can however forbid a re-implantation; otherwise, a multiple use of the expensive infusion devices would be perfectly possible.

Thus at the present the target group of patients is very limited on cost grounds, and chiefly includes pain therapy in the final stages.

In an advanced version of an infusion device without an electrical energy storage unit, different throttle paths can be combined together (German Laid-Open Patent Application DE-OS 4,123,091), whereby it is possible to set different flow rates. This is achieved by means of a mechanical bistable element, which is set with a key by hand before implantation. The adjustment can also take place after implantation, by a minor operation. The element adjustments then become accessible from outside through a small cut, and the implant itself can remain in the body.

From German Laid-Open Patent Application DE-OS 3,247,232, an infusion system for the supply of medicament is known in which the implanted infusion appliance has a memory device for operating information, able to transmit the stored data to a remote measuring device outside the body of the patient who has an implanted infusion appliance. This remote measuring device and the infusion appliance both have a transmitter and a receiver, so that an instruction for a remotely controlled readiness for operation can be transmitted to the infusion appliance from an instruction transmitting device which is exterior of the body. In the system, various operating data can be interrogated from outside, and the infusion rates can be varied from outside. For this purpose, the infusion appliance has various sensors to monitor the operating data, and a pump which operates in a pulse mode.

From East German Patent DD-PS 293,055, an electromagnetically controlled bistable device is known for implantable infusion pumps which are operated by propellant gas, and which have a bistable device with opposed adjacent operating states. Energy supply here takes place inductively from outside. The bistable device then permits only the two operating states, OFF and ON.

From European Patent EP-PS 0,019,814, a control device for infusion appliances is known, in which control signals are coded in the implanted appliance housing of the infusion appliance.

From European Laid-Open Patent Application EP-OS 0,110,117, there is known an implantable microinfusion pump system, which includes a pump with pulse operation.

From European Patent EP-PS 0,031,850, there is known an implantable, magnetically controlled system for the infusion of pharmaceuticals or medicaments into a living body, with a pressure-actuated apparatus for the delivery of pharmaceuticals, and having a movable bistable element.

From European Patent EP-PS 0,039,124, an implantable infusion appliance which has a flow limiter is known.

From European Patent EP-PS 0,128,703, a micropump for implantation is known, and has an ON/OFF element as a flow controller which is normally closed and which is actuated from an external electromagnet.

SUMMARY OF THE INVENTION

The invention has as its object to provide a process for the adjustment of a switchable, flow-limiting apparatus, and an apparatus operating according to the process, the time of use of which is not limited by an electrical energy storage unit, and in which a change of the operating setting, and hence a change in the flow rate, is possible by means of the apparatus, without direct bodily contact with the apparatus.

This object is achieved by means of a service device that is spatially separated and not in bodily connection with the flow-limiting apparatus. According to the process, energy needed for adjustment of the flow-limiting device is transmitted from the service device. The flow-limiting device is switched to adjust its operating setting only during the duration of the energy transmission.

By means of the procedure of adjustment according to the invention, an optimum safety of adjustment (particularly for infusion devices) is achieved, without any necessity for dispensing with the advantageous possibility of adjustment itself, and respectively without a direct bodily contact with the apparatus being necessary for the adjustment.

All of the advantages of the electronically controlled apparatuses are obtained, without it being possible for any inadvertent, uncontrolled adjustment of the flow rate to happen.

The range of variation which is available for the setting of the different flow rates, and the related number of required devices for limiting flow rates in a spatially limited equipment, can be optimized by multistable, flow-limiting valves.

The adjustment of the flow-limiting apparatus can be made even more secure if the external feed of energy takes place only intermittently. The feed of energy then advantageously always takes place when an adjustment of the flow rate limiting apparatus is to be undertaken.

When the setting of different flow rates (e.g., for medicaments from a supply container) takes place by means of different throttle paths arranged following the flow-limiting apparatus, the flow rate can no longer be changed after a setting of the flow-limiting apparatus, until the next adjustment of the flow-limiting apparatus. This procedure thus provides increased security in operation. This is of great importance, particularly for infusion devices.

The multistable, flow-limiting apparatus can advantageously be realized in that a piston is moved in the interior of the flow-limiting apparatus, that the piston has two stable end positions, and that a third positionally stable state of the piston is attained by the combination of magnetic holding force and a restoring spring force.

It is very advantageous for operating security and life if the flow-limiting apparatus remains in its stable positions without drawing current.

It is advantageous if the external feed of energy takes place inductively. This energy feed is cost-favorable and requires relatively little space for its realization. This is of particular importance for infusion devices.

It is very advantageous if data transmission exists, into and out of the device with the flow-limiting apparatus. For this purpose, a data transmission device must be provided in the device and in an external service appliance. This makes possible a data transmission from within the device, e.g., of data intermediately stored in an EEPROM, to the service appliance. However, other data, which are determined outside the device with the flow-limiting apparatus are passed on to the device, also to be transmitted to the exterior. This means, for an implanted infusion device, that the data from the interior of the patient's body can be transmitted outside the patient's body.

It is advantageous, in the us of the flow-limiting apparatus in an infusion device, if the state of filling of the supply contained in the infusion device is measured and these data are intermediately stored in the infusion unit in an electronic memory. EEPROMs are particularly suitable as electronic memories, since they require no energy to maintain the memory contents.

In the infusion device, a pressurized gas reservoir is particularly suitable as the liquid forwarding device, and exerts a pressure on the supply container in the direction of the flow-limiting apparatus. This pressurized gas reservoir has the advantage of very high operating security with a relatively small space requirement.

Advantageous arrangements are described in the claims and especially in the description of the drawings.

It is also very advantageous if the device with the flow-limiting apparatus has an electronic circuit. This serves, in particular, for data transmission, if necessary for data determination, if necessary for data storage, and if necessary also for the preprocessing of the data which have been determined.

Advantageous arrangements of the electronic circuit are described in the claims and especially in the description of the drawings.

BRIEF DESCRIPTION OF THE DRAWINGS

The invention will be explained in more detail below, with reference to the drawings, in connection with which further features of importance to the invention will be explained. The use of the flow-limiting apparatus in an infusion device will be described there by way of example, although the invention is not to be limited to the use of the apparatus in such a device.

In the Figures:

FIG. 1 shows an infusion device with a flow-limiting apparatus according to the invention;

DETAILED DESCRIPTION OF PREFERRED EMBODIMENTS

Figure 3:
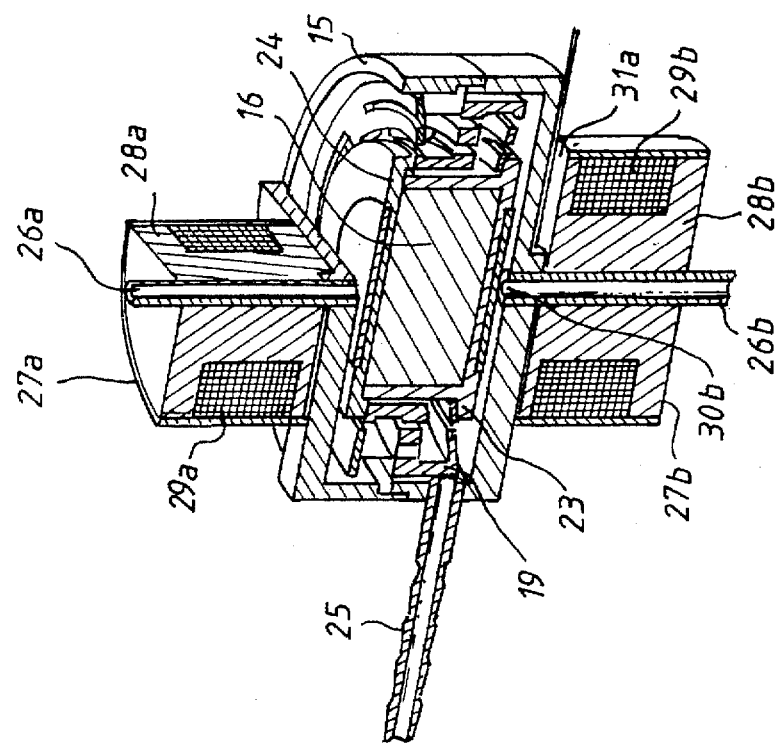
FIG. 3 shows a perspective view of the section through the apparatus as shown in FIG. 2.

The infusion pump (1) shown in FIG. 1 has a septum (2), through which a medicament can be filled into the supply container (3) with a hypodermic needle (not shown in the Figure) through the abdominal wall, when the infusion pump (1) has been implanted into the body of a patient. The supply container (3), which acts as the medicament chamber, is bounded by a bellows (4) which expands on filling. This bellows (4) consists of titanium. The nearly constant excess pressure of the propellant gas in the pressurized gas reservoir (5) exerts a pressure on this bellows (4), leading in the course of time to an emptying of the medicament from the supply container (3). The pressurized gas reservoir (5) is bounded laterally by a partition (9), and is dimensioned such that the gas exerts a nearly constant pressure on the supply container (3) for the whole time while this is being emptied.

A sewing eyelet (10) is fitted laterally on the housing of the infusion pump (1); at it, the infusion pump (1) is sewn firmly to the surrounding tissue, so that during the duration of the implantation the infusion pump (1) does not change its position too much and thereby cause pain to the wearer.

The throttle paths (7: 7.11; 7.12; 7.21; 7.22) limit the quantity of medicament which can be delivered per unit time from the supply container. These throttle paths (7) begin behind the valve (6: 6.1; 6.2), which opens or closes the throttle paths (7) for medicament flow. The throttle paths (7)

all end in a bolus septum (11) and have an outlet there via a catheter (12) into the interior of the body. The physician can also inject directly into this bolus septum (11), in order to administer an additional dose of medicament to the wearer of the infusion pump (1).

The septum (2) and the bolus septum (11) project out of the housing of the infusion pump (1), so that the physician can feel the two septa (2, 11) when searching for them.

In the septum (2), a needle stop (8) ensures that the injection needle (not shown in the drawing) is not damaged while the supply container (3) is being filled.

The outlet of the medicament from the infusion pump (1) takes place through the throttle paths (7) which are connected following the valve (6), so that a constant flow rate is reached. An inlet from the supply container (3) goes into each of the two valves (6.1 and 6.2), and two throttle paths (7.11 and 7.12; 7.21 and 7.22) lead out from each valve (6.1 and 6.2). The flow rate then depends on the gas pressure and in addition primarily on the length of the throttle paths (7) and on their capillary diameter.

If several throttle paths (7) are used, different flow rates can be achieved by the parallel and/or serial connection of various throttle paths (7). The changeover then takes place by means of a tri-stable electromechanical microvalve (6). This valve (6) is explained in more detail in the following FIGS. 2, 3 and 4.

Figure 2:
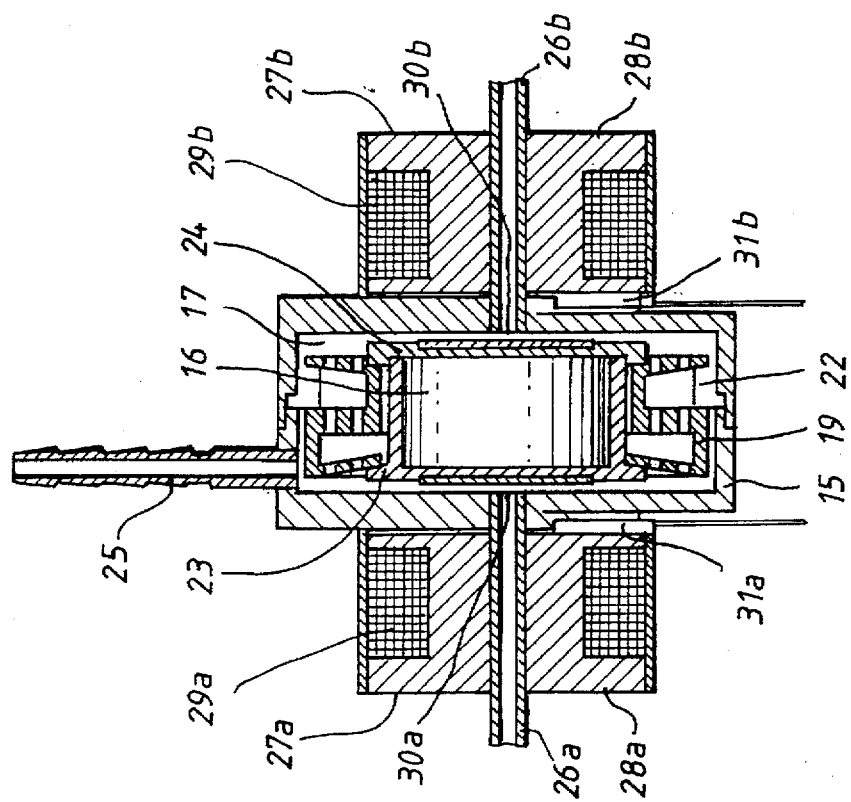
FIG. 2 shows a section through the flow-limiting apparatus.
Figure 4:
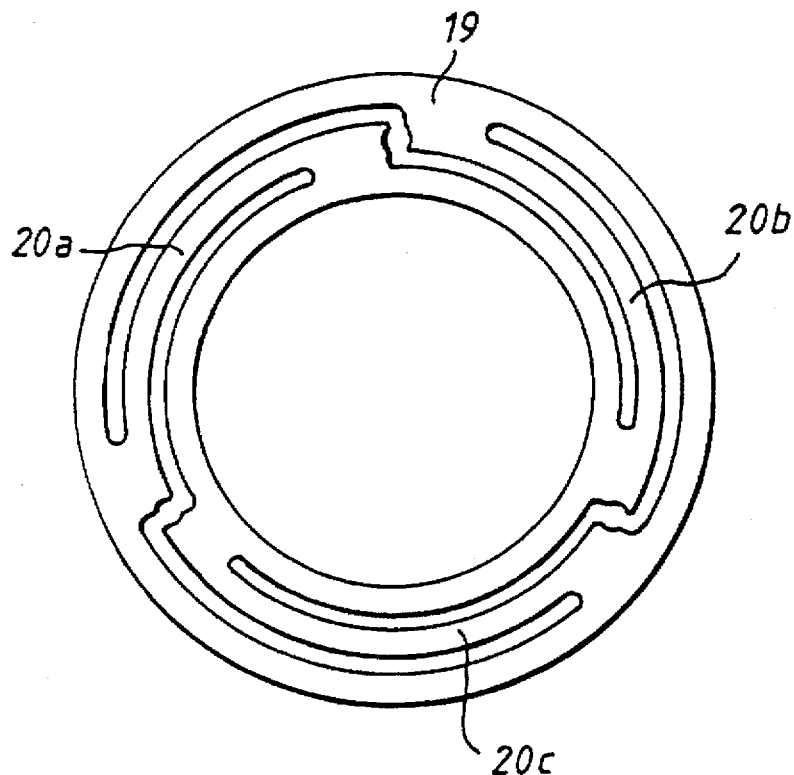
FIG. 4 shows the spring element from the apparatus, in top view.

In FIG. 2 there is shown a section through a electromechanical valve (15), having three stable operating positions and in FIG. 3, a view of a section through the valve (15). The piston (16) consists of a permanent magnet material (e.g., Vacodym), and is encapsulated with a material (e.g., titanium) of the encapsulation (23, 24) which is compatible (i.e., not reacting) with the medicaments used. The fastening of the piston (16) consists of a spring element (19) (see FIGS. 4 and 5).

The spring element (19) of FIG. 2 centers, and likewise guides, the piston (16) within the valve chamber (17).

Figure 5:
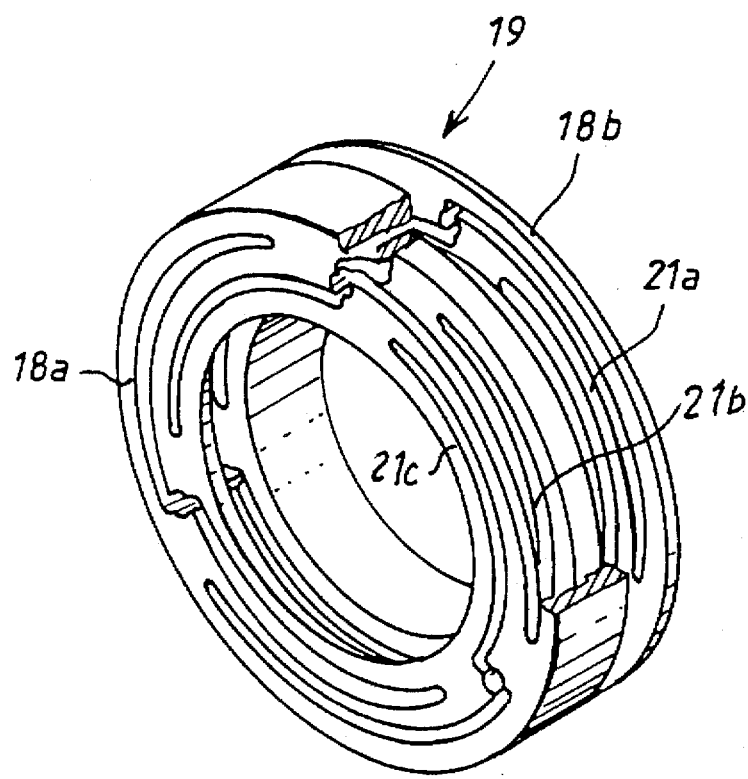
FIG. 5 shows the spring element of FIG. 4, represented in perspective.

The leaf springs of FIG. 5, which run in two planes (18a, 18b) exert a prestress which is respectively directed towards the center and which makes possible a stable middle position of the piston (16). The prestresses are produced by the deformation of the spring element (19) during mounting. The mounting ring (22) spreads a portion of the spring element (21a, b and c), thus producing a force component on the piston (16) in the positive Z-direction (up direction according to Cartesian coordinates). The leaf springs (20a, b and c) are prestressed inwards by the encapsulation (23, 24) of the piston as in FIG. 2, so that a force is produced in the negative Z-direction (down direction according to Cartesian coordinates). On motion of the piston in the negative or positive Z-direction, dependent on direction, respective leaf springs of the one plane are relieved of stress and in the other plane are further stressed, or vice versa.

The valve chamber (17) has a lateral inlet (25) and, arranged on the end faces, two opposed, central outlets (30a, 30b), to each of which is fitted a respective capillary connection (26a, 26b) to the throttle paths (7).

A respective electromagnet (27a, 27b), with a coil former (28a, 28b) of low retentivity magnetic material, is seated on each end face of the valve chamber (15). By correct poling of the two coils (29a, 29b), the permanent magnetic piston (16) can be moved out of its middle position which is defined by the leaf springs (20a, b, c; 21a, b, c) towards the +Z direction or the -Z direction. When the piston (16) has been completely pulled into a position at one end of its path, one of the two outlets (30a, 30b) is closed. After the current is switched off, this position of the valve (15) is still maintained. The required holding forces are produced by the permanent magnet piston (16) and the magnetization which it produces of the respective coil formers (28a, 28b) of the electromagnets (27a, 27b). The dimensions are to be made such that the permanent magnetic holding force is greater than the restoring force of the leaf springs (20a, b, c; 21a, b, c).

The position at any given time of the valve (15) is determined by sensors (31a, 31b) which are sensitive to magnetic fields, and which are built in on the end face on the side of the electromagnets (27a, 27b) facing the valve chamber (17). A maximum field strength is then set in the end positions for the sensor concerned (31a, 31b).

In the middle position (M) defined by the leaf springs (20a, b, c; 21a, b, c), the field strength is about equal for both end position sensors (31a, 31b). This middle position can be achieved by a dynamically controlled adjustment of the valve (15). It is possible to bring the piston (16) into the middle position by means of the built-in sensors (31a, 31b) by means of a suitable control electronics, (e.g., a PI controller, in which the flux through both magnetic field sensors is equal in the middle position: $\Phi_1=\Phi_2 \rightarrow \Phi_1-\Phi_2=0$ (reference value for the controller)). After the electromagnets (27a, 27b) are switched off, this state is still maintained, since the spring force dominates the magnetic attractive forces, which then scarcely differ.

The piston (16) can be directed into its stable positions by the orientation of the current through the coils (29a, 29b) of the two electromagnets (27a, 27b). Here at any given time one of the two capillary connections (26a, 26b) at the two outlets (30a, 30b) is closed or opened, in an end position of the piston (16). In the middle position, both capillary connections (26a, 26b) are opened.

Figure 6:
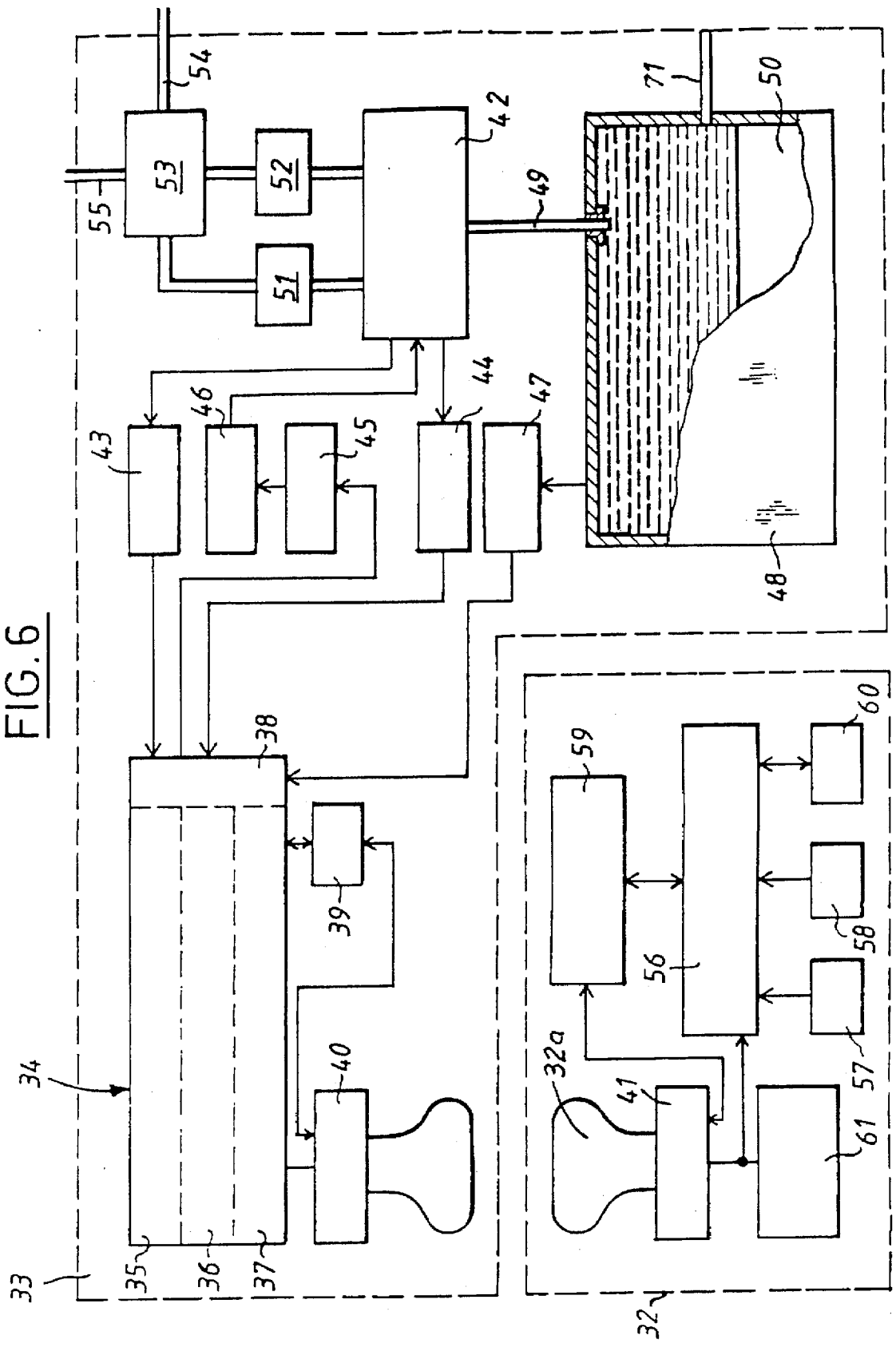
FIG. 6 shows a diagram of the components contained in the service appliance and in the infusion device.

The extracorporeal service appliance (32) and the implanted infusion device (33) are shown schematically in FIG. 6.

The infusion device (33) has an electronic control device (34) which controls all activities in the infusion device (33). This control device (34) consists essentially of an EEPROM (35), a single chip computer (36), a serial interface (37) (a parallel interface would also be conceivable, but without advantage), and a port (38) to which various drivers and sensors can be connected.

The serial interface (37) is connected to a modulator/demodulator (39) for the absorption telemetry (40). This absorption telemetry (40) consists of a LF/RF converter and serves for communication between the infusion device (33) and the extracorporeal service appliance (32). The same antenna serves both for energy transmission and also for bidirectional data transmission.

There is contained in the service appliance (32) a coil (32a) via which energy can be inductively transmitted into the infusion device (33). The transmitted energy is used to operate the single chip computer (36), the sensors, (43, 44) the driver (45) and the valve (42). Energy coupling takes place only in the presence of the extracorporeal service appliance (32).

Two sensors (43, 44) are connected to the port (38) of the single chip computer (36) and ascertain the position of the valve (42). The mode of operation of these sensors (43, 44) has already been explained in connection with FIGS. 2, 3 and 4.

Moreover a driver (45) for a valve changeover unit (46) is connected to the port (38). The position of the valve (42) can thus be changed by means of a corresponding instruction, received from the service appliance (32) by the receiver in the absorption telemetry (40) and transmitted via the serial interface (37) to the single chip computer (36). The corresponding control characteristic is produced by the single chip computer (36) and correspondingly acts on the changeover unit (46).

Furthermore a filling level sensor (47) is connected to the port (38) of the single chip computer (36), and transmits to the single chip computer (36) a message concerning the level, i.e., concerning the quantity of medicament which is still present in the supply container (48). The single chip computer (36) calculates therefrom the infusion time still available and tests whether the amount of flow agrees with the values which have been set. Additionally, the physician can add fluid into the supply container 48 via a needle 71.

A duct (49) leads from the supply container (48) to the valve (42). The supply container (48) is constructed as a bellows and is constantly under the pressure of a pressurized gas reservoir (50). The pressure exerted by the pressurized gas reservoir (50) on the supply container (48) drives the medicament contained in this in the direction towards the valve (42).

Two throttle paths (51, 52) lead from the valve (42). The throttle paths (51, 52) ensure that the supply container (48) empties only in a controlled manner. They consist of capillaries, and the quantity of liquid flowing through them per hour is dependent on the pressure difference over the throttle paths (51, 52), on their capillary length, and on the capillary diameter of the individual throttle paths (51, 52); this diameter can be different for each throttle path (51, 52). The valve (42) opens both throttle paths (51, 52) or only one. As long as the position of the valve (42) is not changed, the quantity of liquid delivered per hour remains constant.

The two throttle paths (51, 52) end in the bolus (53), at the outlet of which is located a catheter (54) into the interior of the body of the wearer of the implanted infusion device (33). The physician can also inject a medicament directly into the bolus (53) with an injection needle (55).

The service appliance (32) has a transformer (41) as a component of the absorption telemetry (40) for the inductive transmission of energy to the infusion device (33). This transformer (41) is supplied by a battery (61). The battery (61) is also connected to a microcontroller 56 (36).

An operator, who will normally be a physician, can by means of a keyboard (57) or by means of function keys (58) interrogate from the infusion device (33) the operating data determined by the single chip computer (36) in the infusion device (33), or can initiate an adjustment of the valve (42) in the infusion device (33). For this purpose, the service appliance (32) has a data communication device (59), which consists of a modulator and demodulator for the absorption telemetry (40). All the operating parameters transmitted from the infusion device (33), and also the instructions sent to it, can be displayed on a LCD display (60).

The service appliance (32) thus performs two tasks. Firstly, energy is inductively transmitted from the service appliance (32) into the implanted infusion device (33) when the service appliance (32) is brought into the vicinity of the infusion device (33) (abdominal wall). During the transmission of energy, the valve (42) can be controlled from the service appliance (32) by means of an absorption telemetry which is located both in the service appliance (32) and in the infusion device (33). A single chip computer (36) is mounted in the infusion device (33), effects the communication with the service appliance (32), and can change over as prescribed, and control the functioning of, the internal valve (42) having three stable operating positions located in the infusion device (33).

No electrical energy is stored in the infusion device (33) in order to change over the valve (42). In order to change over the valve (42) contained in the infusion device (33), energy has to be transmitted inductively into the infusion device (33).

If the service device (32) is moved away, the inductive coupling is broken and the implanted infusion device (33) becomes without current, so that an adjustment of the valve (42) cannot take place. The flow rate which has been set is however still maintained, since the valve or valves (42), connected in series or in parallel, remain in their stable operating position(s). The possibilities of variation of the flow rate can thus be greatly increased by the use of several valves (42).

When the infusion device (33) is activated (i.e., energy is transmitted from the extracorporeal service device (32)), the filling level can be measured by means of a sensor (47). From the level and the flow rate which has been set, the remaining time to the next filling can be indicated for the patient on the display (60) of the service appliance (32). The monitoring of the flow rate can then advantageously be determined by means of stored level values. EEPROMs which permanently store the level values are particularly suitable here.

From the adjustability and the filling level measurement, and the possibilities resulting from these, a flexibility results which was otherwise reserved to the electronic infusion devices, but without having to accept the disadvantage of the greatly limited life due to battery operation.

An absolute insensitivity of the final electrically controlled valve (42) to interference from external interfering effects is achieved by the realization of the energy coupling according to the invention. In contrast to this, in infusion devices in which the adjustment of the valve takes place by means of the current of an electrical storage device (i.e., with a permanent electrical supply, e.g., a battery), there is always the danger that these infusion devices are reprogrammed by interference effects from the exterior.

In the infusion device (33) according to the invention, a doubled security is achieved. In the first place, the infusion device (33) is passive in the normal state. Apart from this, data transmission is effected, for security reasons, by means of absorption telemetry. Additional security against interfering pulses is realized by an additional coding of the data and instructions to be transmitted. Moreover, the absorption telemetry is only effective at close range.

We claim:

1. Process for adjustment of a switchable, flow-limiting device inside a patient's body having at least three stable operating states for limited flow of liquids or gases by means of a service device outside said patient's body, said flow-limiting device and said service device being spatially separated with no bodily connection between said service device and said flow-limiting device comprising:

establishing different flow rates for said liquids or gases by means of different throttle paths arranged to follow said flow-limiting device in a device that includes said flow-limiting device, and, transmitting energy needed for adjustment of said flow-limiting device from said service device into said device that includes said flow-limiting device, thereby switching said flow-limiting device among said at least three stable operating states to switch said flow of said liquids or gases from one throttle path arrangement to another only during a duration of said energy transmission.

2. Process for the adjustment of a switchable flow-limiting device according to claim 1, wherein said device that includes said flow-limiting device is an infusion pump for implantation into a patient's body for treatment of the patient with medicament, said infusion pump having at least one puncture point for filling a supply container to store a selected medicament, further comprising:
- transporting said selected medicament from said supply container to said flow-limiting device by means of a liquid transporting arrangement, and
- introducing said selected medicament from said supply container into said patient's body by means of said throttle paths.

3. Process for the adjustment of a switchable, flow-limiting device according to claim 2, further comprising measuring filling-level values of said supply container with a sensor and storing said filling-level values intermediately in a memory in said infusion pump.

4. Process for the adjustment of a switchable, flow-limiting device according to claim 1, wherein said switchable flow-limiting device comprises a valve having at least three stable positional operating states.

5. Process for the adjustment of a switchable, flow-limiting device according to claim 1, wherein said energy transmitting step comprises transmitting energy only intermittently.

6. Process for the adjustment of a switchable, flow-limiting device according to claim 1, wherein said switching step comprises moving a piston within said flow-limiting device between two stable end positions in an interior of said flow-limiting device and a third stable position achieved by combination of magnetic holding force and restoring spring force.

7. Process for the adjustment of a switchable, flow-limiting device according to claim 6, further comprising retaining said switchable, flow-limiting device in said stable positions without drawing electric current.

8. Process for the adjustment of a switchable, flow-limiting device according to claim 1, wherein said energy transmitting step comprises transmitting said energy inductively.

9. Process for the adjustment of a switchable, flow-limiting device according to claim 1, further comprising transmitting intermediately stored data from an interior of an infusion pump that includes said flow-limiting device to said service device by means of a data transmission device having portions located in said infusion pump and in said service device.

10. Process for the adjustment of a switchable, flow-limiting device according to claim 1, wherein said energy transmitting step comprises transmitting energy inductively by means of absorption telemetry.

11. Apparatus for adjustment of the flow of liquids or gases inside a patient's body, comprising:
- a device inside said patient's body including a flow-limiting device,
- and a service device outside said patient's body that enables switching of said flow-limiting device,
- wherein said flow-limiting device is a switchable flow-limiting device having at least three stable operating states,
- said flow-limiting device and said service device being spatially separated with no bodily connection between said flow-limiting device and said service device,
- a plurality of throttle paths arranged to follow said flow-limiting device in said device that includes said flow-limiting device, and
- a device for transmitting energy needed for adjustment of said flow-limiting device from said service device to switch said flow of said liquids or gases from one throttle path arrangement to another only during the duration of energy transmission from said service device,
- said flow-limiting device comprising a piston in a chamber within said flow-limiting device and an integrated leaf spring structure for mounting and guiding said piston,
- said piston being stable in three positional operating states, and
- said chamber having at least one lateral intake and at least two end faces with a central opposed outlet on each of said at least two end faces.

12. Apparatus according to claim 11, wherein said piston comprises a permanent magnet further comprising a separately acuatable electromagnet having a coil former on each side of said at least two end faces.

* * * * *